United States Patent [19]

Nakamura et al.

[11] Patent Number: 5,665,586
[45] Date of Patent: Sep. 9, 1997

[54] **PROTEASE FROM *STREPTOMYCES FRADIAE***

[75] Inventors: Etsuo Nakamura, Kobe; Hiroshige Tsuzuki, Tsuzuki-gun; Kengo Kitadokoro, Minoo; Masaru Shin, Kobe; Hiroshi Teraoka, Sakai, all of Japan

[73] Assignee: Shionogi & Co., Ltd., Osaka, Japan

[21] Appl. No.: 343,428

[22] PCT Filed: Apr. 30, 1993

[86] PCT No.: PCT/JP93/00592

§ 371 Date: Nov. 18, 1994

§ 102(e) Date: Nov. 18, 1994

[87] PCT Pub. No.: WO93/23530

PCT Pub. Date: Nov. 25, 1993

[30] Foreign Application Priority Data

May 19, 1992 [JP] Japan ................. 4-126511

[51] Int. Cl.$^6$ .................. C12N 9/52; C12N 9/50; C12N 1/00; C12N 1/20
[52] U.S. Cl. .................. 435/220; 435/219; 435/896
[58] Field of Search .................. 435/219, 220

[56] References Cited

PUBLICATIONS

C. Carmona & G. Gray, "Nucleotide Sequence of the Serine Protease Gene of *Staphylococus aureus*, Strain V8", *Nucleic Acids Res.*, 15, p. 6757 (1987).

G. Drapeau et al., "Purification and Properties of an Extracellular Protease of *Staphylococus aureus*", *J. Biol. Chem.*, 247, pp. 6720–6726 (1972).

T. Komiyama et al., "Replacement of P$_1$ Leu$^{18}$ by Glu$^{18}$ in the Reactive Site of Turkey Ovomucoid Third Domain Converts It into a Strong Inhibitor of Glu–specific *Streptomyces griseus* Proteinase (GluSGP)", *J. Biol. Chem.*, 266, pp. 10727–10730 (1991).

K. Nagata et al., "Subsite Mapping of an Acidic Amino Acid–Specific Endopeptidase from *Streptomyces griseus*, GluSGP, and Protease V8", *J. Biochem.*, 110, pp. 859–862 (1991).

T. Niidome et al., "Purification and Characterization of an Acidic Amino Acid–Specific Endopeptidase of *Bacillus subtilis* Obtained from a Commercial Preparation (Protease Type XVI, Sigma)", *J. Biochem.*, 108, pp. 965–970 (1990).

I. Svendsen & K. Breddam, "Isolation and Amino Acid Sequence of a Glutamic Acid Specific Endopeptidase from *Bacillus licheniformis*", *Eur. J. Biochem.*, 204, pp. 165–171 (1992).

I. Svendsen et al., "The Primary Structure of the Glutamic Acid–Specific Protease of *Streptomyces griseus*", *FEBS*, 292, pp. 165–167 (1991).

N. Yoshida et al., "Purification and Characterization of an Acidic Amino Acid Specific Endopeptidase of *Streptomyces griseus* Obtained from a Commercial Preparation (Pronase)", *J. Biochem.*, 104, pp. 451–456 (1988).

U. Sinha et al., "Two New Extracellular Serine Proteases From *Streptomyces fradiae*," *Int. J. Biochem.*, 23, pp. 979–984 (1991).

K. Kitadokoro et al., "Purification, Characterization, and Molecular Cloning of an Acidic Amino Acid–Specific Proteinase From *Streptomyces fradiae* ATCC 14544," *Biochim. Biophys. Acta*, 1163, pp. 149–157 (1993).

*Primary Examiner*—Robert A. Wax
*Assistant Examiner*—Lisa J. Hobbs
*Attorney, Agent, or Firm*—Fish & Neave; James F. Haley, Jr.

[57] ABSTRACT

According to the present invention, a novel protease derived from *Streptomyces fradiae* for cleaving the C-terminal of a glutamic acid residue in an amino acid sequence of a polypeptide and a production method for this protease from *Streptomyces fradiae* are provided, and the characteristics of this protease are made clear. Further, DNA sequences for encoding this protease and a prepropeptide are also made clear. The protease specific to glutamic acid can be used for a variety of purposes including analysis of a protein and cleavage of a peptide chain at a desired site in a fusion protein.

3 Claims, 2 Drawing Sheets

FIG. 1

```
          1
(SFase)  VAGGDAIYGG  GSRCSAAFNV  TKNGVRYFLT  AGHCTNLSST  WSSTSGGTSI
(SGPE)   .L..G.....  ..........  ..G.A...V.  ......I.AN  ..AS...SVV 51
         GVREGTSFPT  NDYGIVRYTT  TTNVDGRVNL  YNGGYQDIAS  AADAVVGQAI
         ..........  .........D  GSSPA.T.D.  ...ST...S.  ..N.......

101
         KKSGSTTKVT  SGTVSAVNVT  VNYSDGPVYG  MVRTTACSAG  GDSGGAHFAG
         ..........  ....T.....  ...G....N  .G........  ..........

151                                187
         SVALGIHSGS  SGCTGTNGSA  IHQPVREALS  AYGVNVY
         ..........  ...S..A...  .....TK...  ...T..L
                                                188
```

FIG. 2

PROTEASE FROM STREPTOMYCES FRADIAE

FIELD OF THE INVENTION

The present invention relates to a novel protease for cleaving the carboxyl side of a glutamic acid residue in an amino acid sequence of a polypeptide and a DNA sequence for encoding the protease.

BACKGROUND OF THE INVENTION

As an enzyme for acting on a protein (polypeptide) so as to specifically cleave the carboxyl side of a glutamic acid (Glu) residue, V8 protease derived from *Staphylococcus aureus* V8 strain is known (Gabriel R. Drapeau et al., J. Biol. Chem. 247, 20, 6720–6726 (1972)). This enzyme is classified as a serine protease. C. Carmona et al. (Nucl. Acids Res., 15, 6757 (1987)) cloned a DNA sequence for encoding this enzyme.

A similar enzyme, acidic amino acid specific endopeptidase derived from *Streptomyces griseus*, which is an actinomyces, is also known (Norio Yoshida et al., J. Biochem. 104, 3, 451–456 (1988)). Recently, I. Svendsen et al. reported an amino acid sequence of the acidic amino acid specific endopeptidase purified from *Streptomyces griseus* (FEBS LETTERS 292 165–167 (1991)). Furthermore, glutamic acid specific endopeptidase derived from *Bacillus subtilis* is also known (Takuro Niidome et al., J. Biochem. 108, 965–970 (1990)). With respect to some of these proteases, the characteristics thereof have been studied and inhibitors against them are known (K. Nagata et al., J. Biochem. 110, 859–862 (1991) and T. Komiyama, J. Biol. Chem. 266, 17, 10727–10730 (1991)).

The aforementioned enzymes are useful for specifically cleaving a protein at the aforementioned site for the purpose of structural analysis of the protein; for obtaining an objective protein through cleavage of a fusion protein in the case where the objective protein is desired to be produced as the fusion protein by a genetic recombination technique and the like. In the latter case, for example, after producing the objective protein by coupling with another protein through a Glu residue, the resultant is subjected to cleavage with one of the enzymes. Thus, the objective protein can be separated. Accordingly, there is a demand for a protease having such an enzymatic activity other than the above-mentioned enzymes.

DISCLOSURE OF THE INVENTION

The objective of this invention is providing a novel protease having an enzymatic activity for cleaving the carboxyl side of a Glu residue, and a DNA sequence for encoding the protease.

The present inventors have made various studies to obtain a protease having the activity of an acidic amino acid specific endopeptidase (in particular, a glutamic acid specific endopeptidase) from a strain of a microorganism other than the above-mentioned microorganisms. As a result, they found a novel protease having the above-mentioned characteristic derived from *Streptomyces fradiae*, and studied the characteristics thereof in detail. Furthermore, they determined a DNA sequence for encoding this protease, thereby accomplishing the present invention.

The protease of this invention cleaves a peptide bond including a carboxyl group of a glutamic acid residue in a peptide and has the following characteristics:

(1) an optimal pH: approximately 8.2; and (2) a stable pH range: 6.0 through 9.0 at a temperature of 37° C.

In a preferred embodiment, the protease is derived from *Streptomyces fradiae*.

In a preferred embodiment, the protease is derived from *Streptomyces fradiae* ATCC 14544 strain.

In a preferred embodiment, the protease comprises an amino acid sequence from Val in the 1 position to Tyr in the 187 position of SEQ ID No. 1.

The DNA sequence of this invention encodes any one of the aforementioned proteases. In a preferred embodiment, the DNA sequence comprises a base sequence from G in the 945 position to C in the 1505 position of SEQ ID No. 1.

In a preferred embodiment, the DNA sequence encodes a protease comprising an amino acid sequence from Met in the −170 position to Tyr in the 187 position of SEQ ID No. 1.

In a preferred embodiment, the DNA sequence comprises a base sequence from A in the 435 position to C in the 1505 position of SEQ ID No. 1.

The protease of the invention (hereinafter referred to as the SFase) is produced from Streptomyces, particularly a strain belonging to *Streptomyces fradiae*. For example, it is produced from *Streptomyces fradiae* ATCC 14544 strain available from American Type Culture Collection (ATCC).

PREFERRED EMBODIMENTS FOR PRACTICING THE INVENTION

The present invention will now be described in detail in the order of the procedures.

I. Culture condition:

The SFase of the invention is produced by using *Streptomyces fradiae*, for example, *Streptomyces fradiae* ATCC 14544 strain. In the case of culturing the strain that can produce the SFase, a medium used for the strain is not required to be special, and any ordinary medium can be used. For example, a medium including glucose, soybean meal, yeast extract, corn steep liquor, potato starch and various salts may be used. The medium pH is 5 through 9, and preferably approximately 7.0, and the medium temperature is 15° C. through 50° C., and preferably approximately 28° C. The strain is cultured, for example, aerobically for approximately 3 through 5 days with stirring or shaking. The SFase is mainly secreted extracellularly.

II. Method for harvesting the enzyme:

In order to harvest and purify the SFase of the invention from the culture, one or a combination of known production methods can be used. For example, the culture solution may be centrifuged to obtain a supernatant, which may be purified by an appropriate means, thereby obtaining the enzyme of the invention.

For example, the supernatant may be precipitated with ammonium sulfate. The precipitate may be dissolved in a buffer solution, and the mixture may be subjected to separation by chromatography using S-Sepharose. Then, the resultant may be subjected to affinity chromatography using S-Sepharose again, thereby giving the present enzyme. The characteristics of the enzyme described below was measured by using this enzyme preparation.

III. Method for measuring the activity:

As a substrate, Z-Phe-Leu-Glu-pNA (wherein Z indicates carbobenzoxyl, and pNA indicates a p-nitroaniline residue) is used, and the substrate is dissolved in 50 mM Tris-HCl (pH 7.5, including 2 mM $CaCl_2$ and 2% DMF) so as to achieve a final concentration of 0.2 mM. An enzyme solution is added thereto, and allowed to react at a temperature of 37° C. for 10 minutes. The absorbance of p-nitroaniline released through the enzymatic reaction into the reaction solution is measured at 410 nm. The amount of the enzyme for attaining an absorbance of 1.0 is defined as 1 unit (U).

IV. Characteristics of the enzyme:

The enzymatic and protein chemical characteristics of the SFase of the invention are as follows:

(1) Enzymatic action and substrate specificity:

1. Synthetic substrates listed in Table 1 were prepared and respectively dissolved in 50 mM Tris-HCl (including 2 mM $CaCl_2$, and dimethylformamide (DMF) or dimethyl sulfoxide (DMSO) in the ratio shown in Table 1; pH 7.5) so as to achieve respective concentrations as listed in Table 1. The present enzyme was added thereto to cause a reaction at a temperature of 25° C. By measuring the absorbance (410 nm) of p-nitroaniline released through the enzymatic reaction into the reaction solution, the amount (A410 nm) of p-nitroaniline released per mg each substrate per 1 minute was calculated. The results are listed in Table 1.

TABLE 1

Substrate specificity:

| Substrate | Concentration (final) mM | Solvent(%) | A 410 nm /mg/min |
|---|---|---|---|
| Z—Phe—Leu—Glu—pNA | 0.20 | DMF 0.2 | 319.1 |
| Boc—Ala—Ala—Glu—pNA | 0.20 | DMF 2.0 | 126.2 |
| Boc—Ala—Ala—Asp—pNA | 0.20 | DMF 2.0 | 14.3 |
| Bz—Tyr—pNA | 0.02 | DMF 2.0 | 0*) |
| Z—Trp—pNA | 0.20 | DMF 2.0 | 0*) |
| Bz—Arg—pNA | 0.50 | DMSO 1.0 | 0*) |
| Z—Gly—Ser—pNA | 0.20 | DMF 2.0 | 0*) |
| Suc—Ala—Ala—Ala—pNA | 0.20 | — — | 0*) |
| Z—Ala—Ala—Leu—pNA | 0.125 | DMF 5.0 | 0*) |
| Leu—pNA | 2.00 | — — | 0*) |

Condition: 50 mM Tris-HCl, 2 mM $CaCl_2$, pH 7.5, 25° C.
Detection: A410 nm
DMF: N,N-dimethylformamide
DMSO: dimethy sulfoxide
Z—: benzyloxycarbonyl-
Boc—: t-butoxycarbonyl-
Bz—: benzoyl-
Suc—: succinyl-
pNA: p-nitroanilide
*)No color detected at A410 nm through a reaction for 15 minutes at a concentration of the enzyme of 4.2 μg/ml at a temperature of 23°C.

2. As a proteinous substrate, an oxidized B chain of insulin was selected, and the action of the present enzyme against the substrate was examined. First, the oxidized B chain of insulin was dissolved in 50 mM Tris-HCl, pH 7.5, and the present enzyme was added thereto so as to achieve the enzyme/substrate =1/139 (W/W), and the reaction was effected for a determined period of time. The obtained reaction mixture was subjected to HPLC using a Vydac Protein C4 column, and eluted for 30 minutes by a linear concentration gradient using 0% through 50% acetonitrile in 0.1% TFA. The thus obtained fragments were analyzed with regard to the amino acid sequence. As a result, it was found that a bond between Glu13 and Ala14 alone was cleaved.

From the results of the above described items 1. and 2., it is apparent that the SFase of the invention is a glutamic acid specific endopeptidase for cleaving a peptide bond including carboxyl in a glutamic acid residue in a peptide.

(2) Optimal pH and stable pH range:

As a substrate, Z-Phe-Leu-Glu-pNA was used. The substrate was dissolved in 50 mM buffers including 10% DMF (an acetate buffer (pH 3.2 through 6.1), a phosphate buffer (pH 5.5 through 8.1), a Tris-HCl buffer (pH 6.1 through 9.8) and a glycinate buffer (pH 9.1 through 11.1)). The SFase of the invention was added thereto, and the reaction was effected at a temperature of 25° C. for 10 minutes. The absorbance of p-nitroaniline released through the enzymatic reaction into the reaction solutions was measured at 410 nm. When the reactions were effected in the reaction solutions having various pH, it was found that the optimal pH of the reaction was approximately 8.2.

Next, under various pH conditions, the SFase of the invention was allowed to stand at a temperature of 37° C. for 1.5 hours, and the reactions were effected in accordance with the activity measuring method, thereby measuring the residual activity. As a result, the stable pH range was found to be 6.0 through 9.0.

(3) Effect of an inhibitor:

The effects of various inhibitors on the SFase of the invention are listed in Table 2. The SFase of the invention is completely inhibited by diisopropyl fluorophosphate (DFP), but is not inhibited by ethylenediaminetetraacetic acid (EDTA) and o-phenanthroline (OP), which are inhibitors of metal proteases. From this, the SFase of the invention was found to be classified as a serine protease.

Further, the SFase of the invention is inhibited by neither Tosyl-Lys-chloromethylketone (TLCK) nor Tosyl-Phe-chloromethylketone (TPCK), which are inhibitors of trypsin and chymotrypsin, but is completely inhibited by Boc-Phe-Leu-Glu-chloromethylketone. From this, similarly to the result obtained with regard to the substrate specificity, the SFase of the invention is found to be a glutamic acid specific endopeptidase.

TABLE 2

Inhibition:

| Inhibitor | Concentration of Inhibitor | Residual Activity (%) |
|---|---|---|
| Control | — | 100 |
| Z—Phe—Leu—Glu—CK | 0.5 mM | 0 |
| Boc—Ala—Ala—Ala—CK | 0.5 mM | 102 |
| TPCK | 0.5 mM | 101 |
| TLCK | 0.5 mM | 112 |
| DFP | 2.0 mM | 7 |
| DFP | 0.5 mM | 20 |
| DFP | 0.25 mM | 33 |
| EDTA | 10.0 mM | 126 |
| EDTA | 1.0 mM | 113 |
| EDTA | 0.1 mM | 110 |
| OP | 10.0 mM | 104 |
| OP | 1.0 mM | 108 |
| OP | 0.1 mM | 106 |

Buffer: 50 mM Tris-HCl, 2.0 mM $CaCl_2$, pH 7.5, 25° C.
Preincubation: 37° C., 1 hour
Enzyme: 1.0 μg/ml
Substrate: 0.2 mM Z—Phe—Leu—Glu—pNA, 0.2% DMF (4) Molecular weight:

By SDS-PAGE (15% gel, 1.0 mm; molecular weight marker: RAINBOW™ Protein Molecular Weight Marker manufactured by Amersham), the molecular weight of the present enzyme was measured, and as a result, it was calculated to be 19,000. The molecular weight calculated based on the amino acid sequence determined from the gene sequence of the present enzyme described below is 18,702, which coincides with the value obtained by SDS-PAGE.

(5) Amino acid composition:

The SFase of the invention was hydrolyzed by using 4M methanesulfonic acid [including 0.2% 3-(2-aminoethyl) indole] at a temperature of 110° C. for determined periods of time (24, 48 and 72 hours). The respective hydrolyzed products were analyzed with regard to amino acids by a Hitachi amino acid analyzer (Model 835). The results are listed in Table 3. The amino acid composition determined based on the DNA sequence of the present enzyme (described below) are listed as well. These results apparently coincide with each other.

TABLE 3

Amino acid composition:

|  | Measured Value | Value estimated from cDNA |
|---|---|---|
| Asp | 19.4 | 18 |
| Thr | 21.5 | 21 |
| Ser | 22.9 | 23 |
| Glu | 5.9 | 5 |
| Pro | 2.9 | 3 |
| Gly | 33.5 | 31 |
| Ala | 20.5 | 19 |
| Cys/2 | 4.4 | 4 |
| Val | 18.9 | 20 |
| Met | 1.1 | 1 |
| Ile | 6.1 | 7 |
| Leu | 5.9 | 5 |
| Tyr | 10.5 | 10 |
| Phe | 4.3 | 4 |
| Lys | 4.0 | 4 |
| His | 3.8 | 4 |
| Arg | 7.1 | 7 |
| Trp | 0.9 | 1 |
| Res | — | 187 |
| Mol | — | 18702.4 |

(6) Partial sequence of the amino acid:

1. N-terminal amino acid sequence:

The amino acid sequence around the N-terminal was analyzed by using a 477A Protein Sequencer manufactured by Applied Biosystems. In the analysis, the present enzyme was previously inhibited by DFP. The amino acid sequence from the N-terminal to the 31 residue (corresponding to the amino acids from Val in the 1 position to Ala in the 31 position of SEQ ID No. 1) is shown in Table 4.

TABLE 4

N-terminal sequence:

| Step | Amino Acid | pmol | Step | Amino Acid | pmol |
|---|---|---|---|---|---|
| 1 | Val | 2615.1 | 17 | Ala | 1048.6 |
| 2 | Ala | 1771.8 | 18 | Phe | 995.6 |
| 3 | Gly | 2175.8 | 19 | Asn | 670.1 |
| 4 | Gly | 2378.4 | 20 | Val | 1080.1 |
| 5 | Asp | 1097.2 | 21 | Thr | 660.4 |
| 6 | Ala | 2195.4 | 22 | Lys | 410.8 |
| 7 | Ile | 2180.3 | 23 | Asn | 455.1 |
| 8 | Tyr | 1341.4 | 24 | Gly | 979.0 |
| 9 | Gly | 1014.5 | 25 | Val | 1054.4 |
| 10 | Gly | 2154.5 | 26 | Arg | 647.2 |
| 11 | Gly | 2227.4 | 27 | Tyr | 464.9 |
| 12 | Ser | 430.6 | 28 | Phe | 396.5 |
| 13 | Arg | 304.6 | 29 | Leu | 514.0 |
| 14 | x | x | 30 | Thr | 280.3 |
| 15 | Ser | 443.0 | 31 | Ala | 580.5 |
| 16 | Ala | 1002.9 |  |  |  |

TABLE 4-continued

N-terminal sequence:

| Step | Amino Acid | pmol | Step | Amino Acid | pmol |
|---|---|---|---|---|---|

```
1           11          21          31
VAGGDAIYGGGSR-SAAFNVTKNGVRYFLTA...
```

2. C-terminal amino acid sequence:

The present enzyme previously inhibited by DFP was allowed to react with lysyl endopeptidase. The reaction was effected in a 25 mM Tris-HCl buffer, pH 7.5, by using the inhibited SFase and the lysyl endopeptidase at a ratio of 40:1 at a temperature of 24° C. for 6 hours. Each of the obtained fragments was subjected to HPLC using a Vydac protein C4 column (4.6×25 cm), and separated by linear concentration gradient using 20% through 60% of $CH_3CN$ in 0.1% TFA under various conditions. As a result of the analysis of the fragments, a fragment having no basic amino acid at a terminal of the peptide was found, and this fragment was identified as a peptide at the C-terminal. The amino acid composition at the C-terminal (corresponding to the amino acids from Glu in the 177 position to Tyr in the 187 position of SEQ ID No. 1) is listed in Table 5. Further, a sequence assumed to be present within the SFase was also obtained (listed in Table 6; corresponding to the amino acids from Tyr in the 68 position to Arg in the 75 position of SEQ ID No. 1).

TABLE 5

C-terminal sequence:

| Step | Amino Acid | pmol |
|---|---|---|
| 1 | Glu | 760.5 |
| 2 | Ala | 1176.9 |
| 3 | Leu | 1318.5 |
| 4 | Ser | 353.0 |
| 5 | Ala | 1126.6 |
| 6 | Tyr | 934.0 |
| 7 | Gly | 839.0 |
| 8 | Val | 1047.5 |
| 9 | Asn | 603.4 |
| 10 | Val | 955.5 |
| 11 | Tyr | 951.4 |

```
1         11
...EALSAYGVNVY
```

TABLE 6

Sequence of SFase (unknown region):

| Step | Amino Acid | pmol |
|---|---|---|
| 1 | Tyr | 1843.5 |
| 2 | Thr | 2375.8 |
| 3 | Thr | 2266.2 |
| 4 | Thr | 2713.1 |
| 5 | Thr | 2921.1 |
| 6 | Asn | 1460.9 |
| 7 | Val | 2003.5 |
| 8 | Asp | 1896.5 |
| 9 | Gly | 1047.4 |
| 10 | Arg | 620.4 |

TABLE 6-continued

Sequence of SFase (unknown region):

| Step | Amino Acid | pmol |
|------|------------|------|
| 1    | 10         |      |
| ...YTTTTNVDGR... | | |

V. Determination of a DNA sequence for encoding the SFase:

The terms used in the description of the present invention are defined as follows:

An "oligonucleotide" indicates a short single-stranded DNA, and can be chemically synthesized by a known method. The oligonucleotide used in the present invention is chemically synthesized through purification by Gel chromatography using a Sephadex G50 column and high-performance liquid chromatography (HPLC) using a reverse phase silica gel column, if not mentioned otherwise.

"PCR" is an abbreviation of polymerase chain reaction, which is a method for enzymatically amplifying a desired region in DNA (Saiki et al., Science, 239, 487–497 (1988)). First, DNA to be amplified is thermally denatured into a single-strand, and the region at the 3' terminal of each of the obtained single-stranded template DNA is annealed with complementary oligonucleotide primers (two types, one of which is a sense strand and the other an antisense strand). Then, using the action of DNA polymerase, DNA chains are extended from the respective primers. By repeating a series of these reactions, the objective DNA can be amplified a hundred thousand through a million times.

A "Southern analysis" indicates a method for determining whether or not an objective gene is included in a DNA fragment obtained through cleavage by a restriction enzyme. For Southern analysis, DNA is first digested with a restriction enzyme that recognizes a specific base sequence in the two-stranded DNA for the cleavage thereof. The obtained digest is subjected to 1% agarose gel electrophoresis, then denaturated through an alkali treatment into a single-strand, and the resultant is placed on a nylon filter to be transfered. An oligonucleotide or a DNA fragment, which is part of the objective gene, is prepared and labeled to be used as a probe. The probe is subjected to hybridization with the single-stranded DNA on the nylon filter, thereby analyzing the DNA.

Next, a method for determining a DNA sequence for encoding the SFase of the invention will be described in the order of procedures. The DNA sequence was determined by analyzing a genome DNA of *Streptomyces fradiae* ATCC 14544 strain through a method combining PCR, Southern analysis, a direct sequencing method and the like.

(1) Analysis of an internal sequence of a genome DNA by PCR:

A sequence for encoding the SFase can be obtained, for example, from a genome DNA. For this purpose, a genome DNA of *Streptomyces fradiae* ATCC 14544 strain is first prepared from cultured cells of the strain by a known method (J. Marmur et al., J. Mol. Biol. (1961) 3, 208–218). The obtained genome DNA is used as a template DNA for PCR. An oligonucleotide primer used in PCR can be synthesized by a general method based on the amino acid sequence around the N-terminal of the purified enzyme obtained in the above-mentioned item IV (6); and the amino acid sequence of a peptide obtained by partially decomposing the enzyme. For example, an oligonucleotide for encoding the amino acid sequence in the 1 position through 8 position on the N-terminal side of the SFase, i.e., Val Ala Gly Gly Asp Ala Ile Tyr, (up to the second base of a triplet for encoding Tyr at the C-terminal; 23-mer) is chemically synthesized to be used as a sense primer SF1. Since *Streptomyces fradiae* is known to be GC rich, a primer (SEQ ID No. 2) including only one kind of an oligonucleotide is selected to be used without considering degeneracy.

Separately from the above, a peptide having the highest reliability is selected among the peptides that are obtained by partially decomposing the purified enzyme with lysyl endopeptidase and sequenced, and an oligonucleotide is synthesized based on the selected peptide. As is described in Example 2 below, since a sequence of Tyr Thr Thr Thr Thr Asn Val Asp is obtained, a 24-mer complementary to the oligonucleotide for encoding this amino acid sequence is chemically synthesized to be used as an antisense primer SF2 (SEQ ID No. 3).

By conducting PCR using template DNA, the sense primer SF1 and the antisense primer SF2, the objective DNA chain in the genome DNA is extended and amplified. The obtained PCR product is analyzed through agarose gel electrophoresis, thereby obtaining a DNA fragment having a length of approximately 220 bp. This DNA fragment is introduced into an appropriate vector to conduct subcloning, and then the DNA sequence is determined by a chain terminator method (Proc. Natl. Acad. Sci. USA Vol. 74, 5463–5467 (1977)). As a result, a DNA sequence of 225 bp is determined, and it is found that the amino acid sequence Tyr Thr Thr Thr Thr Asn Val Asp, which is used as a base for producing the antisense primer SF2, is an amino acid sequence positioned in the 68 position through 75 position.

(2) Southern analysis of the genome DNA:

The genome DNA derived from *Streptomyces fradiae* ATCC 14544 strain prepared in the above-mentioned item (1) is double-digested with restriction enzymes SalI and PstI, and the resultant is subjected to agarose gel electrophoresis for separation. Then, the obtained DNA fragments are blotted on a nylon membrane filter for Southern analysis. As a probe for hybridization, the PCR product of the SF1-SF2 of item (1), which was previously labeled with $^{32}$p-dCTP by a general method, is used. Positive DNA fragments hybridized with this probe are exhibited as a band of 2.0 kb.

(3) Determination of a base sequence of the genome DNA of the SFase:

The genome DNA of *Streptomyces fradiae* ATCC 14544 strain obtained in item (1) is cleaved with an appropriate restriction enzyme, the resultant is introduced into an appropriate vector, and the DNA base sequence of the SFase is determined by the chain terminator method mentioned in item (1).

For example, the genome DNA of *Streptomyces fradiae* ATCC 14544 strain obtained in item (1) is digested with SalI and PstI. The DNA fragment of approximately 2 kb confirmed in item (2) is subcloned with M13mp10 previously treated with the same restriction enzymes, and a plaque hybridization is conducted. At this point, as a probe, the probe for hybridization used in the Southern analysis of item (2) can be used. Plasmid DNA is isolated from the plaque which is found to be positive through plaque hybridization, and a DNA sequence of the inserted fragment of this plasmid is determined. As a result of the DNA sequencing, the DNA sequence of 2064 bp shown in SEQ ID No. 1 is determined, and SFase is found to comprise a DNA sequence for encoding a prepropeptide comprising amino acids of 170 residues including methionine encoded by a translation initiation codon ATG and a mature peptide comprising amino acids of 187 residues. Upstream, by eight bases, from ATG in the −170 position included in the 5' non-translation region, a sequence AAGGAG of a ribosome binding region is present. Further upstream, a −10 region and a −35 region both including a promoter-like sequence are found. On the 3' side of the DNA sequence for encoding methionine, a basic amino acid specific to a signal peptide is present, to which a hydrophobic amino acid is subsequent. Further, Ala-X-Ala (wherein X indicates an optional amino acid), which is a signal peptide recognition sequence, is also present. Thus, it is found that a typical signal peptide is constructed.

Figure 1:
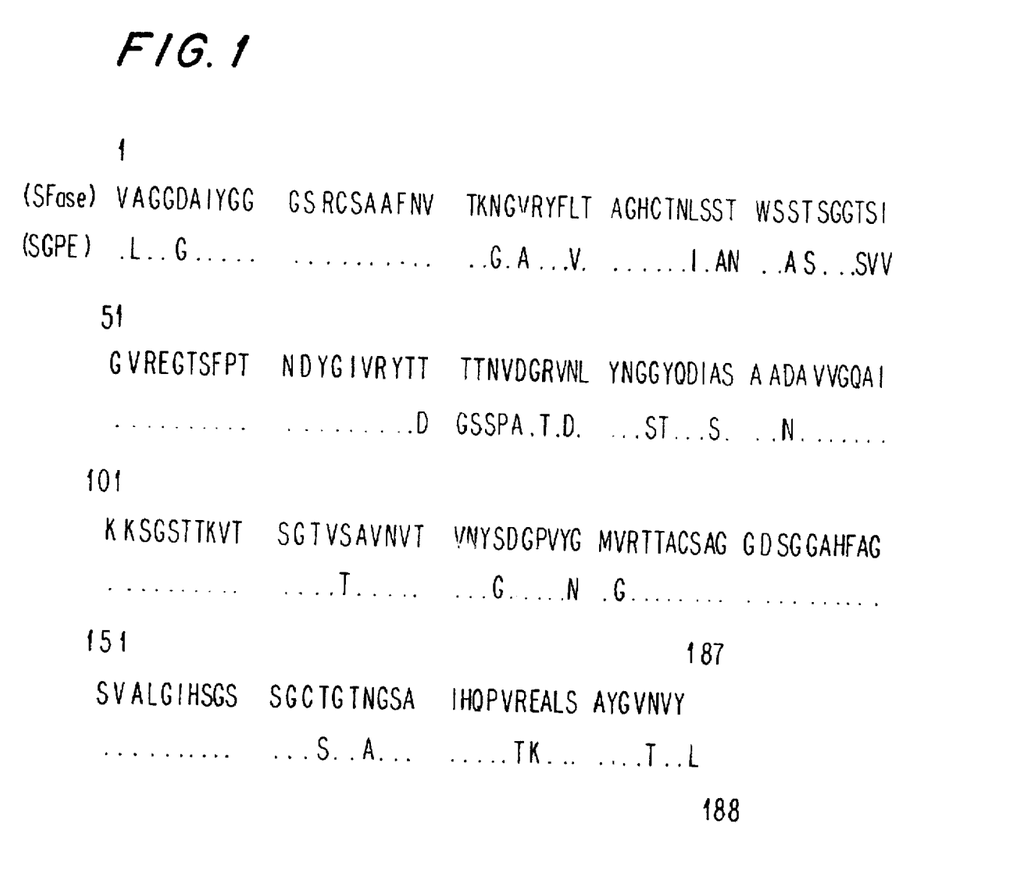
FIG. 1 shows the comparison in the amino acid sequences between a mature peptide of SFase of the invention (upper lines) and a mature peptide of the same kind of an enzyme derived from *Streptomyces griseus* (lower lines). The portions shown with dots indicate the same amino acids.

I. Svendsen et al. (described above) reported an amino acid sequence, of the same type, of an enzyme derived from *Streptomyces griseus*. When the amino acid sequence of this enzyme is compared with that of the SFase of the invention, the homology is found to be 81.3%. FIG. 1 shows the comparison between the amino acid sequences of the mature peptides of these two enzymes. The letters used in FIG. 1 indicate the ordinary amino acids each with one letter. I. Svendsen et al., however, did not perform gene cloning, and hence, the precursor, the promoter sequence and the like are unknown.

The present invention provides a novel protease for specifically cleaving the C-terminal of a glutamic residue in the amino acid sequence of a polypeptide and a DNA sequence for encoding the protease. This protease can be prepared by culturing *Streptomyces fradiae* or by chemical synthesis. Such a protease can be used for a variety of purposes including analysis of a protein and cleavage of a peptide chain at a desired site in a fusion protein. The DNA sequence for encoding the protease can be used to produce and detect the protease.

EXAMPLES

The present invention will now be described by way of examples.

Example 1

(Harvest of the SFase)

*Streptomyces fradiae* ATCC 14544 strain was cultured in a medium having pH 7.0 and including 3% potato starch, 1% soybean meal, 0.5% corn steep liquor, 0.5% glycerol, 0.3% NaCl, 0.35% $CaCO_3$ and 0.1% yeast extract at a temperature of 28° C. for 3 through 5 days (K. Morihara et al., Biochem. Biophys. Acta., 139(1967) 382–397). The obtained culture solution was centrifuged (at 8000 rpm for 30 minutes) to obtain a supernatant by removing the fungi. 60% Saturated ammonium sulfate was added to the obtained supernatant, thereby precipitating a protein. The thus obtained precipitate was centrifuged ( at 8000 rpm for 30 minutes), and the collected precipitate was dissolved in 10 mM Tris-HCl, pH 7.5, including 2 mM $CaCl_2$. Then, the obtained mixed solution was dialyzed using the same buffer solution as an outer solution. Next, the dialysis inner solution was lyophilized to obtain crude enzyme powder. Then, 104.4 g of the crude enzyme powder was suspended in 1.2 L of 5 mM Tris-HCl, pH 7.5, and the resultant was dialyzed again by using 20 L of the same type of the buffer solution as an outer solution for 20 hours. The obtained dialysis inner solution was centrifuged (at 8000 rpm for 20 minutes), thereby obtaining a solution of 1.3 L.

To the obtained solution, 1.0 L of S-Sepharose (equilibrated with 5 mM Tris-HCl, pH 7.5) was added, and the obtained mixture was gently stirred at a temperature of 4° C. for 5 hours. Then, the supernatant was discarded, the S-Sepharose having absorbed the enzyme was charged in a glass column (11.2×10 cm) to be washed with approximately 3 L of 5 mM Tris-HCl, pH 7.5, and eluted with 5 mM Tris-HCl, 0.3M NaCl, pH 7.5.

Fractions having SFase activity were eluted from the column, collected (2.3 L), and dialyzed with 5 mM Tris-HCl, pH 7.5, for two days and nights (during which an outer solution of 20 L was exchanged three times). Approximately 2.5 L of the dialysis inner material was allowed to adsorb on approximately 500 ml of S-Sepharose (equilibrated with 5 mM Tris-HCl, pH 7.5) charged in a column (5×25 cm). Then, the column was washed with approximately 2.5 L of the same type of buffer solution as that used in the equilibrium, and eluted with 5 L of a buffer solution, including 0 through 0.1M NaCl, by linear concentration gradient. Then, fractions having SFase activity were collected (eluted at a concentration of approximately 0.05M NaCl; approximately 1000 ml), and dialyzed overnight with 5 mM Tris-HCl, pH 7.5. Next, the dialysis inner material was subjected to affinity chromatography. In the affinity chromatography, approximately 70 ml of CH Sepharose 4B-Phe-Leu-D-Glu-OMe was used as a carrier, which was charged in a column of 2.5×14 cm and equilibrated with 5 mM Tris-HCl, pH 7.5. The dialysis inner material was allowed to be adsorbed upon the column. The column was washed with approximately 500 ml of the same type of buffer solution as that used in the equilibrium, and eluted with 1.0 L of the same type of buffer solution, including 0 through 0.3M NaCl, by linear concentration gradient.

The SFase activity of the collected fractions was measured in accordance with the aforementioned activity measuring method. The SFase activity was found in fractions eluted around the NaCl concentration of 0.25M. The thus obtained fractions having SFase activity were collected (0.2 L), and dialyzed for 24 hours using 5 mM Tris-HCl, pH 7.5, as an outer solution (20 L×2). Approximately 320 ml of S-Sepharose charged in a column of 3.2×40 cm was equilibrated with 5 mM Tris-HCl, pH 7.5, and the obtained dialysis inner material was allowed to be adsorbed upon the column. Next, the column was washed with approximately 1.5 L of the same type of buffer solution as that used in the equilibrium, and eluted with 4 L of buffer solution, including 0 through 0.1M NaCl, by linear concentration gradient.

Figure 2:
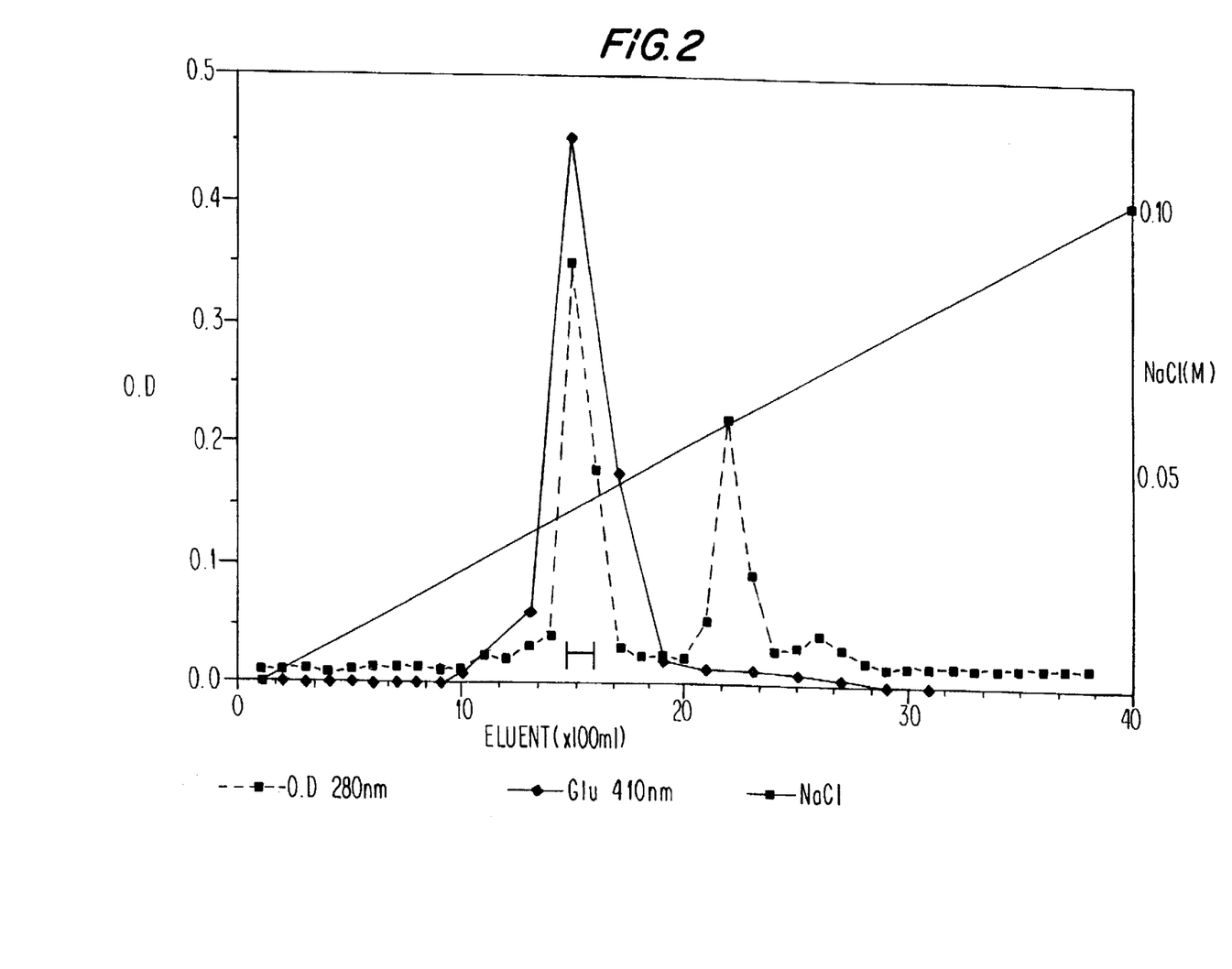
FIG. 2 shows an elution pattern of the SFase from S-Sepharose.

The SFase activity of the collected fractions was measured in accordance with the aforementioned activity measuring method. Further, the absorbance of each fraction at 280 nm was measured to be used as a criterion for a protein concentration. Both results are shown in FIG. 2. As is apparent from FIG. 2, the SFase activity was found in fractions eluted at a NaCl concentration of approximately 0.05M (200 ml). The obtained fractions were dialyzed for 40 hours using 5 mM Tris-HCl, pH 7.5 (20 L each was exchanged three times) as an outer solution to be used as a preserved solution. The thus obtained SFase exhibited a single band in SDS-PAGE. From 104.4 g of the crude enzyme powder, approximately 3.0 mg of the enzyme was obtained (quantified using a Bio Rad Protein assay kit).

Example 2

(Sequencing of DNA for encoding the SFase)

(1) Analysis of an internal sequence of a genome DNA by PCR:

A genome DNA was prepared from cultured cells of *Streptomyces fradiae* ATCC 14544 strain by the method of J. Marmur (described above), and the obtained DNA was used as a template DNA for PCR. An oligonucleotide primer to be used in PCR was produced based on a determined amino acid sequence of part of the SFase produced from *Streptomyces fradiae* ATCC 14544 strain. First, an oligonucleotide for encoding the amino acid sequence in the 1 position through 8 position on the N-terminal side of the SFase, i.e., Val Ala Gly Gly Asp Ala Ile Tyr, (up to the second base of a triplet for encoding Tyr at the C-terminal; 23-mer) was chemically synthesized to be used as a sense primer SF1. Since *Streptomyces fradiae* is known to be GC rich, a primer (SEQ ID No. 2) including only one kind of oligonucleotide was selected to be used without considering degeneracy.

Next, the purified SFase obtained in Example 1 (after DEP treatment) was allowed to react with lysyl endopeptidase (manufactured by Wako Pure Chemical Industries, Ltd.) at a temperature of 37° C. for 5 hours. The resultant digest with the enzyme was decomposed and purified by high-performance liquid chromatography using a Vydac protein C4, 300A column (4.6×25 cm). The amino acid sequences of the thus obtained digested fragments were checked with a 477 type protein sequencer manufactured by Applied Biosystems. The amino acid sequence of one of the fragments was Tyr Thr Thr Thr Thr Asn Val Asp. Then, a 24-mer complementary to the oligonucleotide for encoding this amino acid was chemically synthesized to be used as an antisense primer SF2 (SEQ ID No. 3).

By using the template DNA, the sense primer SF1 and the antisense primer SF2, the DNA was amplified by the PCR method [Saiki et al., Science 239, 487–491 (1989)]. When part of the obtained PCR product was analyzed by 1% agarose gel electrophoresis, a DNA fragment of approximately 220 bp was found. This DNA fragment was isolated, blunted through a treatment by a Klenow fragment, and subcloned with M13mp10 previously treated with SmaI. Then, the DNA sequence was determined by the chain terminator method (Sanger et al.; described above). As a result, a DNA sequence of 225 bp was determined, and the amino acid sequence corresponding to the antisense primer SF2 was found to be positioned in the 68 position through the 75 position.

(2) Southern analysis of the genome DNA:

The genome DNA derived from *Streptomyces fradiae* ATCC 14544 strain prepared in item (1) was double-digested with the restriction enzymes SalI and PstI, and the resultant was subjected to 1% agarose gel electrophoresis. Then, the obtained DNA fragments were blotted on a nylon membrane filter, and Southern analysis was conducted. As a probe for hybridization, the PCR product of the SF1-SF2 of item (1) corresponding to the amino acid sequence from the 38 position to the 45 position of the SFase (SEQ ID No. 4; a probe SF3) was labeled with $^{32}$P-2ATP by a general method. Positive DNA fragments hybridized with this probe were exhibited as a band of 2.0 kb.

(3) Determination of a base sequence of the genome DNA of the SFase:

The DNA fragments of approximately 2 kb obtained by digesting, with SalI and PstI, the genome DNA of *Streptomyces fradiae* ATCC 14544 strain obtained in item (1) were treated with the same type of restriction enzymes, and then ligated to dephosphorylated M13mp10. The ligation was performed by using a commercially available kit (manufactured by Takara Shuzo Co., Ltd.).

Next, plaque hybridization was conducted. At this point, the probe SF3 used in item (2) was used as a probe. Plasmid DNA was isolated from the plaque which was found to be positive through plaque hybridization, and the DNA sequence of the inserted fragment of this plasmid was determined by the aforementioned chain terminator method. As a result of the DNA sequencing, the DNA sequence of 2064 bp was determined. The sequence is shown in SEQ ID No. 1.

Through study of the DNA sequence of the SFase determined in the above-mentioned manner, it was found to comprise a DNA sequence for encoding a prepropeptide comprising amino acids of 170 residues including methionine encoded by a translation initiation codon ATG and a mature peptide comprising amino acids of 187 residues. Upstream, by eight bases, from ATG in the −170 position included in the 5' non-translation region, a sequence AAG-GAG of a ribosome binding region was present. Further upstream, a −10 region and a −35 region both including a promoter-like sequence were found. On the 3' side of the DNA sequence for encoding the methionine, a basic amino acid specific to a signal peptide was present, to which a hydrophobic amino acid was subsequent. Further, Ala-X-Ala (wherein X indicates an optional amino acid), which is a signal peptide recognition sequence, was also present. Thus, it was found that a typical signal peptide was constructed.

We claim:

1. A protease derived from *Streptomyces fradiae* for cleaving a peptide bond including a carboxyl group of a glutamic acid residue in a peptide and having the following characteristics:

(1) an optimal pH: approximately 8.2; and (2) a stable pH range: 6.0 through 9.0 at a temperature of 37° C.

2. A protease according to claim 1 derived from *Streptomyces fradiae* ATCC 14544 strain.

3. A protease for cleaving a peptide bond including a carboxyl group of a glutamic acid residue in a peptide and having the following characteristics:

(1) an optimal pH; approximately 8.2; and (2) a stable pH range; 6.0 through 9.0 at a temperature of 37° C., comprising an amino acid sequence from Val in the 1 position to Tyr in the 187 position of SEQ ID No. 1.

\* \* \* \* \*

SEQUENCE LISTING ( 1 ) GENERAL INFORMATION:

( i i i ) NUMBER OF SEQUENCES:4

( 2 ) INFORMATION FOR SEQ ID NO:1:

( i ) SEQUENCE CHARACTERISTICS:
( A ) LENGTH: 2064
( B ) TYPE: nucleic acid
( C ) STRANDEDNESS: double
( D ) TOPOLOGY: linear ( i i ) MOLECULE TYPE: Genomic DNA ( i v ) ORIGINAL SOURCE:
( A ) ORGANISM: Streptomyces fradiae ( i x ) FEATURE:
( A ) NAME/KEY: -35 signal
( B ) LOCATION: 359..364

( C ) IDENTIFICATION METHOD: by experiment
( D ) NAME/KEY: -10 signal
( E ) LOCATION: 378..383
( F ) IDENTIFICATION METHOD: by experiment
( G ) NAME/KEY: CDS
( H ) LOCATION: 435..1505
( I ) IDENTIFICATION METHOD: by experiment
( J ) NAME/KEY: sig peptide
( K ) LOCATION: 435..944
( L ) IDENTIFICATION METHOD: by experiment ( x i ) SEQUENCE DESCRIPTION: SEQ ID NO:1:

| | | |
|---|---|---|
| GTCGACCGGC GCCGTGGTCG GCCAGCAGCC TTCGGCGGCG GCCGCGTCCG GCACCAACGA | 60 |
| CAAGGCCGGC GCCCCGCAGA ACCTGATGCG CTGGACGCTG ACCCGCGCCA TCAAGGAGAC | 120 |
| GCTGGTCCCG CCGACCGGGT ACGGCTACCC GCACATGCTG ACGCCCGTGC AGCTGACGCC | 180 |
| CGCCCCGGCC CGTACGCACG GGCCGGCGGG CCGACGCCCC GCCCCGCCGC ACCGCGGCCG | 240 |
| GGCTGCGGCC CGCGAGGCCG CCCCCTGACG CCGCCCCCTT CCGGCCCCCA CGCCGGGAGG | 300 |
| GGGCGGTCTC CATGTCCGGG TCGTCGCGCC GGAGGCCGGG CGCGGCGGAA ACGCGCCCTT | 360 |
| GCGGTCAGTG AAGCGTTCAT GTCAAGTTGC TCCCTCGGTA CGTCCCCACC CGTCACCGAC | 420 |

```
AAGGAGACCC CGGC ATG AGA CGC ACC ACC CGC GCG CGC ACC GGT CTG TCC              470
              Met Arg Arg Thr Thr Arg Ala Arg Thr Gly Leu Ser
              -170          -165              -160

GCC CTG CTC CTC GCC GCC TCC CTC GGC CTC GGC GCC GCC CCG GCC GGA              518
Ala Leu Leu Leu Ala Ala Ser Leu Gly Leu Gly Ala Ala Pro Ala Gly
        -155              -150              -145

GCC GAC GCC CCC CAG AGG CCC GCC CCC ACC CCG GCC TCC GAC TCC GCC              566
Ala Asp Ala Pro Gln Arg Pro Ala Pro Thr Pro Ala Ser Asp Ser Ala
    -140              -135              -130

GCC GCC CTC CAC GCC CTC GAC GCC GCC GTC GAG CGG ACC CTC GGC GAC              614
Ala Ala Leu His Ala Leu Asp Ala Ala Val Glu Arg Thr Leu Gly Asp
    -125              -120              -115

GAC AGC GCC GGC ACC TAC GTG GAC GCC GGC ACC GGC GAA CTC GTC GTC              662
Asp Ser Ala Gly Thr Tyr Val Asp Ala Gly Thr Gly Glu Leu Val Val
-110              -105              -100              -95

ACC GTC ACC ACC GAG GCC GCC GCC GCC AAG GTC CGC GCG GCG GGC GCC              710
Thr Val Thr Thr Glu Ala Ala Ala Ala Lys Val Arg Ala Ala Gly Ala
        -90              -85              -80

ACG CCC CGG CGG GTC CAG CGC GGC GCC GCC GAG CTC GAC GCG GCC ATG              758
Thr Pro Arg Arg Val Gln Arg Gly Ala Ala Glu Leu Asp Ala Ala Met
        -75              -70              -65

GCC GCC CTG GAG GCA CGG GCC AAG ATC CCC GGC ACC TCG TGG GGG CTG              806
Ala Ala Leu Glu Ala Arg Ala Lys Ile Pro Gly Thr Ser Trp Gly Leu
        -60              -55              -50

GAC CCG CGC ACC AAC CGG ATC GCC GTG GAG GCC GAC TCC TCC GTC TCC              854
Asp Pro Arg Thr Asn Arg Ile Ala Val Glu Ala Asp Ser Ser Val Ser
    -45              -40              -35

GCC CGC GAC CTG GCC CGG CTC CGC AAG GTC GCC GCC TCC CTC GAC GGC              902
Ala Arg Asp Leu Ala Arg Leu Arg Lys Val Ala Ala Ser Leu Asp Gly
-30              -25              -20              -15

GCC GTC AGC GTC ACC CGC GTC CCC GGC GTG TTC CAG CGC GAG GTG GCC              950
Ala Val Ser Val Thr Arg Val Pro Gly Val Phe Gln Arg Glu Val Ala
            -10              -5                    1

GGC GGC GAC GCC ATC TAC GGC GGC GGC TCG CGC TGC TCG GCG GCC TTC              998
Gly Gly Asp Ala Ile Tyr Gly Gly Gly Ser Arg Cys Ser Ala Ala Phe
            5              10              15

AAC GTC ACC AAG AAC GGC GTT CGG TAC TTC CTG ACC GCC GGG CAC TGC             1046
Asn Val Thr Lys Asn Gly Val Arg Tyr Phe Leu Thr Ala Gly His Cys
        20              25              30

ACC AAC CTC TCG TCC ACC TGG TCG TCC ACC TCC GGC GGC ACG TCC ATC             1094
```

-continued

| | | | | Thr | Asn | Leu | Ser | Ser | Thr | Trp | Ser | Ser | Thr | Ser | Gly | Gly | Thr | Ser | Ile | |
| --- | --- | --- | --- | --- | --- | --- | --- | --- | --- | --- | --- | --- | --- | --- | --- | --- | --- | --- | --- | --- |
| | | | | 35 | | | | | 40 | | | | | 45 | | | | | 50 | |
| GGC | GTC | CGC | GAG | GGC | ACC | AGC | TTC | CCG | ACC | AAC | GAC | TAC | GGC | ATC | GTC | | | | | 1142 |
| Gly | Val | Arg | Glu | Gly | Thr | Ser | Phe | Pro | Thr | Asn | Asp | Tyr | Gly | Ile | Val | | | | | |
| | | | | 55 | | | | | 60 | | | | | 65 | | | | | | |
| CGC | TAC | ACG | ACC | ACG | ACC | AAC | GTG | GAC | GGC | CGG | GTC | AAC | CTG | TAC | AAC | | | | | 1190 |
| Arg | Tyr | Thr | Thr | Thr | Thr | Asn | Val | Asp | Gly | Arg | Val | Asn | Leu | Tyr | Asn | | | | | |
| | | | 70 | | | | | 75 | | | | | 80 | | | | | | | |
| GGC | GGC | TAC | CAG | GAC | ATC | GCC | TCC | GCG | GCC | GAC | GCC | GTC | GTG | GGC | CAG | | | | | 1238 |
| Gly | Gly | Tyr | Gln | Asp | Ile | Ala | Ser | Ala | Ala | Asp | Ala | Val | Val | Gly | Gln | | | | | |
| | | 85 | | | | | 90 | | | | | 95 | | | | | | | | |
| GCC | ATC | AAG | AAG | AGC | GGC | TCC | ACG | ACC | AAG | GTC | ACC | AGC | GGC | ACC | GTC | | | | | 1286 |
| Ala | Ile | Lys | Lys | Ser | Gly | Ser | Thr | Thr | Lys | Val | Thr | Ser | Gly | Thr | Val | | | | | |
| | 100 | | | | | 105 | | | | | 110 | | | | | | | | | |
| AGC | GCC | GTC | AAC | GTC | ACC | GTC | AAC | TAC | AGC | GAC | GGC | CCC | GTC | TAC | GGC | | | | | 1334 |
| Ser | Ala | Val | Asn | Val | Thr | Val | Asn | Tyr | Ser | Asp | Gly | Pro | Val | Tyr | Gly | | | | | |
| 115 | | | | | 120 | | | | | 125 | | | | | 130 | | | | | |
| ATG | GTC | CGC | ACG | ACC | GCC | TGC | TCC | GCC | GGC | GGC | GAC | AGC | GGC | GGC | GCC | | | | | 1382 |
| Met | Val | Arg | Thr | Thr | Ala | Cys | Ser | Ala | Gly | Gly | Asp | Ser | Gly | Gly | Ala | | | | | |
| | | | 135 | | | | | 140 | | | | | 145 | | | | | | | |
| CAC | TTC | GCC | GGT | TCC | GTC | GCC | CTC | GGC | ATC | CAC | TCG | GGC | AGC | TCC | GGC | | | | | 1430 |
| His | Phe | Ala | Gly | Ser | Val | Ala | Leu | Gly | Ile | His | Ser | Gly | Ser | Ser | Gly | | | | | |
| | | | 150 | | | | | 155 | | | | | 160 | | | | | | | |
| TGC | ACG | GGC | ACC | AAC | GGC | TCC | GCC | ATC | CAC | CAG | CCG | GTC | CGC | GAG | GCC | | | | | 1478 |
| Cys | Thr | Gly | Thr | Asn | Gly | Ser | Ala | Ile | His | Gln | Pro | Val | Arg | Glu | Ala | | | | | |
| | | 165 | | | | | 170 | | | | | 175 | | | | | | | | |
| CTG | AGC | GCC | TAT | GGC | GTG | AAC | GTG | TAC | TGACCCGCCC | CGCCCGGCCG | | | | | | | | | | 1525 |
| Leu | Ser | Ala | Tyr | Gly | Val | Asn | Val | Tyr | | | | | | | | | | | | |
| | 180 | | | | | 185 | | | | | | | | | | | | | | |

| | | | | | |
| --- | --- | --- | --- | --- | --- |
| GGCGGAGTGC | CACAGTGGGC | GGTATGAGTG | ATCGTCTCCA | TACCGCCCAC | ACCTACGAGC | 1585 |
| TGGCACCGGC | CGTGCTCGCC | TCGATCCGCG | CCCTCCTCCA | GGACGCCTTC | GAAGGCGACC | 1645 |
| TGAGCGAGGA | GGACTGGGAG | CACGGCCTCG | GCGGCGTCCA | CGCGTACGCC | GAGGACCGCG | 1705 |
| GCGGGCGGAT | CGTGGCGCAC | GGCAGCGTCG | TCATGCGCCG | CGTGGTCCAC | GCCGGGCGCG | 1765 |
| CCCACCGCGT | CGGGTACGTG | GAGGCCGTGG | GCGTACGGGC | GGACCGCCGC | CGCCAGGGGC | 1825 |
| TGGGCACGCG | GGTGATGGCG | GCGCTGGAGG | AGGTCCTCGA | CGGGGCGTAC | GACTTCGGCG | 1885 |
| CGCTCTCCGC | CTCCGACGCG | GGCGCCCTGC | TCTAGCTCGC | GCGGCTGGCA | CCTGTGGAAC | 1945 |
| GGCCGCATCG | AGGCGTACGG | CCCGCACGGG | GTGGTCCGGA | TGGCGGACGA | GGAGGACTGC | 2005 |
| ACCTTCCTCG | GCCCTCGGCG | GGCCGCCCGC | TGCCCGCGCC | GGAGGGCGGT | CCCCTGCAG | 2064 |

( 2 ) INFORMATION FOR SEQ ID NO:2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear     ( i i ) MOLECULE TYPE: other nucleic acid, synthesized DNA     ( x i ) SEQUENCE DESCRIPTION: SEQ ID NO:2:

GTCGCCGGCG GCGACGCCAT CTA      23

( 2 ) INFORMATION FOR SEQ ID NO:3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear (  i  i  ) MOLECULE TYPE: other nucleic acid, synthesized DNA (  x  i  ) SEQUENCE DESCRIPTION: SEQ ID NO:3:

GTCCACGTTG GTGGTGGTGG TGTA 24

( 2 ) INFORMATION FOR SEQ ID NO:4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear     ( i i ) MOLECULE TYPE: other nucleic acid, synthesized DNA     ( x i ) SEQUENCE DESCRIPTION: SEQ ID NO:4:

TCGTCCACCT GGTCGTCCAC CTCC 24